United States Patent [19]

Laguzza

[11] Patent Number: 4,675,322

[45] Date of Patent: Jun. 23, 1987

[54] 1-SUBSTITUTED-6-N-PROPYL-8β-METHYLTHIO-METHYLERGOLINES

[75] Inventor: Bennett C. Laguzza, Indianapolis, Ind.

[73] Assignee: Eli Lilly and Company, Indianapolis, Ind.

[21] Appl. No.: 679,832

[22] Filed: Dec. 10, 1984

[51] Int. Cl.[4] .............................................. A61K 31/48
[52] U.S. Cl. ....................................... 514/288; 546/67
[58] Field of Search ................... 546/67; 514/215, 288

[56] References Cited

U.S. PATENT DOCUMENTS

| | | | |
|---|---|---|---|
| 3,901,894 | 8/1975 | Kornfeld | 260/285.5 |
| 4,166,182 | 8/1979 | Kornfeld | 546/67 |
| 4,180,582 | 12/1979 | Kornfeld | 424/61 |
| 4,202,979 | 5/1980 | Kornfeld | 546/67 |
| 4,246,265 | 1/1981 | Kornfeld | 424/61 |
| 4,348,391 | 9/1982 | Stütz et al. | 546/68 |
| 4,348,392 | 9/1982 | Fehr et al. | 546/68 |
| 4,563,461 | 1/1986 | Cohen et al. | 514/288 |

FOREIGN PATENT DOCUMENTS

| | | | |
|---|---|---|---|
| 234137 | 11/1983 | Fed. Rep. of Germany | 546/67 |
| 628895 | 3/1982 | Switzerland | 546/67 |
| 1290203 | 9/1972 | United Kingdom | 514/88 |

OTHER PUBLICATIONS

Smidrkal, et al., "I Subtitled Ergoline Derivatives," Chem Abst. 96:143148X.
Fuller et al., Life Sci, 24, 375 (1979).

Primary Examiner—Nicholas S. Rizzo
Assistant Examiner—Cecilia Shen
Attorney, Agent, or Firm—Bruce J. Barclay; Leroy Whitaker

[57] ABSTRACT

N-1-substituted-6-n-propyl-8β-methylthio-methylergoline, D-2 agonists without interaction with alpha adrenergic receptors.

2 Claims, No Drawings

1-SUBSTITUTED-6-N-PROPYL-8β-METHYLTHIO-METHYLERGOLINES

BACKGROUND OF THE INVENTION

Compounds based on the ergoline ring system:

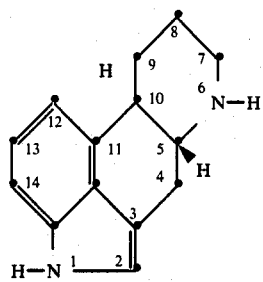

have a surprising variety of pharmaceutical activities. For example, many of the naturally occurring amides of lysergic acid, which is 8β-carboxy-6-methyl-9-ergolene, have valuable and unique pharmacologic properties. The trivial name "ergoline" is given to the above structure and the 9,10-double bonded compound—related to lysergic acid—is called a 9-ergolene rather than a 9,10-didehydroergoline. The name D-ergoline is used herein in naming specific compounds. The letter "D" indicates that the C-5 -carbon atom configuration has the absolute stereochemistry designated as R and that the hydrogen is β—above the plane of the ring system. However, modern usage has tended to omit the "D", on the ground that the newly synthesized ergolines or ergolenes are universally derivatives of natural products such as lysergic acid or elymoclavine, both of which have the R sterochemical—"D" series—configuration and in which the stereochemical integrity at C-5 is maintained during various synthetic procedures. In the ergolines, the C-10 hydrogen is alpha—below the plane of the ring, the C-5 C-10 ring junction being trans. It should be understood that all of the compounds disclosed herein have the R or β stereochemical configuration at C-5, whether or not the specific or generic name is preceded by a "D", and the α configuration at C-10.

Among the pharmacologically active amides of lysergic acid are included naturally-occurring oxytoxic alkaloids ergocornine, ergokryptine, ergonovine, ergocristine, ergosine, ergotamine, etc., and synthetic oxytocics such as methergine as well as the synthetic hallucinogen, lysergic acid diethylamide or LSD. The amides of 6-methyl-8-carboxyergoline (dihydrolysergic acid), known generally as the dihydroergot alkaloids, are oxytocic agents of lower potency and also lower toxicity than the ergot alkaloids themselves.

Recently, it has been found by Clemens, Semonsky, Meites, and their various co-workers that many ergot-related drugs have activity as prolactin inhibitors. Ergocornine, dihydroergocornine, 2-bromo α-ergokryptine and D-6-methyl-8-cyanomethylergoline (Semonsky et al U.S. Pat. No. 3,732,231) are examples of such drugs. References embodying some of the newer findings in the field of ergoline and ergoline chemistry include the following: Nagasawa and Meites, *Proc. Soc. Exp't'l. Biol. Med.*, 135, 469 (1970); Lutterbeck et al., *Brit. Med. J.*, 228, (July 24, 1971); Heuson et al., *Europ. J. Cancer*, 353 (1970); *Coll. Czech. Chem. Commun.*, 33, 577 (1968); *Nature*, 221, 666 (1969); Seda et al., *J. Reprod. Fert.*, 24, 263 (1971); Mantle and Finn, id, 441; Semonsky and co-workers, *Coll. Czech. Chem. Comm.*, 36, 2200 (1971); Schaar and Clemens, *Endocr.*, 90, 285–8 (1972); Clemens and Schaar, *Proc. Soc. Exp. Biol. Med.*, 139, 659–662 (1972), Bach and Kornfeld, *Tetrahedron Letters*, 3225 (1974) and Sweeney, Clemens, Kornfeld and Poore, 64th Annual Meeting, American Association for Cancer Research, April 1973. Recently issued patents in the field of ergolines or of lysergic acid derivatives include the following: U.S. Pat. No. 3,923,812, U.S. Pat. No. 3,929,726, U.S. Pat. No. 3,944,582, U.S. Pat. No. 3,934,772, U.S. Pat. No. 3,954,988, U.S. Pat. No. 3,957,785, U.S. Pat. No. 3,966,739, U.S. Pat. No. 3,968,111, U.S. Pat. No. 4,001,242. Many other related and older patents can be found in Patent Office Classification Files 260-256.4 and 260-285.5.

U.S. Pat. No. 4,166,182 issued Aug. 28, 1979 (filed Feb. 8, 1978) discloses and claims D-6-n-propyl-8β-methylmercaptomethylergoline, among other compounds. The latter drug has been given the generic name "pergolide" and is present undergoing clinical trial as a prolactin secretion inhibitor and in the treatment of Parkinsonism.

The use of pergolide, among other compounds, as a prolactin secretion inhibitor or in the treatment of Parkinsonism, is claimed in U.S. Pat. No. 4,180,582. The use of the corresponding 8α derivative in treating Parkinsonism is claimed in U.S. Pat. No. 4,246,265. 6-Ethyl(or allyl)-8β-methylthiomethylergolines are claimed in U.S. Pat. No. 4,202,979.

Fuller et al, *Life Sci.*, 24, 375 (1979) discusses the pharmacology of pergolide. The α adrenergic blocking activity of pergolide is summarized in Table 5, page 381.

6-Methyl-8β-methylthiomethylergolines are disclosed and claimed in U.S. Pat. Nos. 3,959,288 and 3,901,894 respectively as prolactin secretion inhibitors.

Dopamine D-2 agonists including pergolide are known to lower blood pressure, but usually at higher dose levels than those at which they can be used to treat Parkinsonism or lower serum prolactin. Many of these compounds are known to interact with α adrenergic receptors at hypotensive dosages.

DESCRIPTION OF THE INVENTION

This invention provides a group of dopamine D-2 agonists capable of lowering blood pressure in mammals at dose levels at which there is no interaction with α receptors. These D-2 agonists have the following structure:

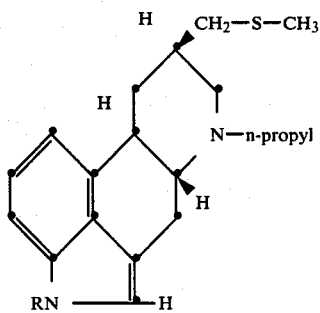

wherein R is 1-propenyl, 2-propenyl (allyl), $C_{1-3}$ alkyl, benzyl or substituted benzyl wherein said substituents are one or two members of the class $C_{1-2}$ alkyl, $C_{1-2}$ alkoxy, hydroxy, Cl, Br, and F, and pharmaceutically-acceptable acid addition salts thereof.

Illustrative of R in the above formula are methyl, ethyl, isopropyl, n-propyl, p-chlorobenzyl, o-methylbenzyl, m-ethylbenzyl, 2,4-dichlorobenzyl, p-fluorobenzyl, 2-methoxybenzyl, 4-ethoxybenzyl, 3-hydroxybenzyl, 3,4-dihydroxybenzyl, 3,4-methylenedioxybenzyl, 4-bromobenzyl, 2,4-dimethylbenzyl and the like.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycollate, malate, tartrate, glucohepanoate, lactobionate, methanesulfonate, propanesulfonate, naphthalene-1-sulfonate, naphthalene-2-sulfonate and the like salts.

Typical compounds coming within the scope of formula I above include

D-1-allyl-6-n-propyl-8$\beta$-methylthiomethylergoline maleate

D-1-(4-chlorobenzyl)-6-n-propyl-8$\beta$-methylthiomethylergoline sulfate

D-1-(3-methoxybenzyl)-6-n-propyl-8$\alpha$-methylthiomethylergoline hydrochloride D-1-(2-ethylbenzyl)-6-n-propyl-8$\beta$-methylthiomethylergoline tartrate D-1-(3,4-methylenedioxybenzyl-6-n-propyl-8$\beta$-methylthiomethylergoline ascorbate D-1-(1-propenyl)-6-n-propyl-8$\beta$-methylthiomethylergoline p-tosylate and the like.

Compounds represented by I above and their pharmaceutically-acceptable salts formed with non-toxic acids are dopamine D-2 agonists capable of lowering an elevated blood pressure in mammals without the occurrence at an effective hypotensive dose level of $\alpha$ receptor interaction. The compounds also have other activities associated with a dopamine D-2 agonist; inhibition of prolactin secretion, effect on turning behavior of dopamine-lesioned rats and on sexual behavior of mammals, etc. The lack of $\alpha$ receptor interaction indicates a greater specificity of the compounds of this invention compared to pergolide. In addition, the compounds have a delayed onset of action, indicating that they may be prodrugs.

Compounds according to formula I are prepared by alkylating a sodium or potassium salt of pergolide with an alkyl or benzyl halide, RX, where X is Cl, Br or I. The reaction is carried out in a mutual inert solvent or suspending agent such as DMF, DMA (dimethylformamide, dimethyl acetamide) and the like at 20°-50° C., preferably at room temperature. First, pergolide, or a salt thereof, is treated with a strong base such as potassium t-butoxide. After the pergolide anion is formed, as indicated by color change or other indicia, the alkyl, alkenyl or benzyl halide is added. If the reaction has not gone to completion within a few hours, as indicated by TLC, additional portions of the base and halide, RX, can be added. Ordinarily, the reaction is carried out at ambient temperature. However, reaction of the pergolide anion and an allyl halide at room temperature results in a derivative in which the double bond has shifted toward the indole-ring nitrogen, thus forming an N-(1-propenyl) derivative. If, however, the reaction is carried out at low temperature, preferably in the range $-30°$ to $-50°$ C., the N-allyl [N-(2-propenyl)] derivative can be isolated. NaH in THF, DMF or dioxan may be used in place of K t-butoxide in the same solvents.

This invention is further illustrated by the following specific examples.

EXAMPLE 1

Preparation of D-1-methyl-6-n-propyl-8$\beta$-methylthiomethylergoline

One gram of pergolide mesylate (D-6-n-propyl-8$\beta$-methylthiomethylergoline methanesulfonate) was slurried in 30 ml of anhydrous DMF (dimethylformamide) at room temperature under a nitrogen atmosphere. The slurry was cooled to about 0° C. with an ice bath, and a solution of 2.09 g of potassium t-butoxide in 10 ml of anhydrous DMF added thereto. The reaction mixture was then removed from the ice bath. After stirring at room temperature for about 20 minutes, the mixture became a yellow solution, indicating a reaction was taking place. After stirring for 45 minutes at room temperature, 167 $\mu$l of methyliodide were added in dropwise fashion using a syringe. The reaction mixture was then stirred at room temperature, becoming a pale orange solution after one hour. The reaction mixture was stirred overnight. An additional 1.09 g of potassium t-butoxide in 10 ml of anhydrous DMF were added followed, after 20 minutes, by an additional 60 $\mu$l of methyliodide. The reaction mixture was stirred at room temperature under N$_2$ for an additional 24 hours at which time TLC of an aliquot of the reaction mixture showed the presence of a new compound. An NMR spectrum on this material (obtained by a standard workup) lacked the downfield N—H peak, indicating substantially complete reaction of the indole nitrogen. The remaining reaction mixture was diluted with 100 ml of dilute sodium hydroxide (pH=11). The resulting cloudy-white mixture was extracted three times with 75 ml portions of methylene dichloride. The combined methylene dichloride extracts were washed twice with 50 ml portions of dil. sodium hydroxide, once with 50 ml of 1N sodium thiosulfate, and once with 50 ml of brine. The methylene dichloride solution was dried and the solvent removed therefrom in vacuo to yield 659 mg of a viscous blue-gray oil. The oil was chromatographed over silica using a 95:5 chloroform/methanol eluant. Fractions containing the desired 1-methyl derivative were combined, and the solvent removed in vacuo. 396 mg of D-1-methyl-6-n-propyl-8$\beta$-methylthiomethylergoline were obtained. The compound crystallized from methanol at $-20°$ C.

The compound (136 mg) was dissolved in a minimum amount of ether at room temperature and 23 $\mu$l of methanesulfonic acid were added. The solvent was removed from the reaction mixture in vacuo. Trituration with ether gave a pale gray solid residue consisting of 78 mg of the methane sulfonate salt of D-1-methyl-6-n-propyl-8β-methylthiomethylergoline. The salt had the following elemental analysis: Calculated: C, 59.40; H, 7.60; N, 6.60; S, 15.10; Found: C, 59.10; H, 7.45; N, 6.43; S, 15.05.

Other compounds prepared by the above procedure included D-1-isopropyl-6-n-propyl-8β-methylthiomethylergoline methanesulfonate; yield 760 mg of base from 1 g of pergolide mesylate; yield of salt=89%. The salt was a tan powder (a monohydrate) with the following elemental analysis: Calculated: C, 58.69; H, 8.14; N, 5.95; S, 13.62; Found: C, 58.50, 58.95; H, 7.98, 7.88; N, 5,88, 6.07; S, 13.76.

D-1-benzyl-6-n-propyl-8β-methylthiomethylergoline methanesulfonate; yield of base=750 mg of a white solid from 1.0 g of pergolide mesylate. The methane sulfonate salt, 48% yield was a white solid melting at 215° C. with decomposition, having the following elemental analysis: Calculated: C, 64.77; H, 7.25; N, 5.59; S, 12.81; Found: C, 64.50; H, 7.30; N, 5.42; S, 13.02.

D-1,6-di-n-propyl-8β-methylthiomethylergoline methanesulfonate; yield of free base=100%; yield of salt=69%. The salt melted with decomposition at 152°–155.5° C. Mass spectrum: M-96 (methanesulfonic acid) 356. Elemental analysis: Calculated: C, 61.03; H, 8.02; N, 6.19; S, 14.17; Found: C, 61.01; H, 8.23; N, 6.18; S, 14.07.

EXAMPLE 2

Preparation of D-1-(1-propenyl)-6-n-propyl-8β-methylthiomethylergoline and D-1-(2-propenyl)-6-n-propyl-8β-methylthiomethylergoline Following the procedure of Example 1, 2 g of pergolide mesylate were converted to the potassium salt of pergolide with potassium t-butoxide in DMF. 465 μl of allyl bromide were added, and the reaction mixture stirred at room temperature for three hours. 580 mg of potassium t-butoxide and 328 mg of allyl bromide were then added, and the reaction mixture stirred for an additional ½ hour at which time TLC indicated that the alkylation had proceeded substantially to completion. As in Example 1, the reaction mixture was quenched with water. The volatile constituents were removed in vacuo, and the resulting residue partitioned between water and methylene dichloride. This aqueous layer was made basic with dilute aqueous sodium hydroxide and extracted again with methylene dichloride. The two methylene dichloride layers were combined, and the combined layers washed with saturated aqueous sodium bicarbonate and then dried. 1.92 g of a brown oily residue were obtained after evaporation of the solvent. The residue was purified by chromatography over SiO$_2$ using an ethyl acetate/hexane eluant containing increasing amounts of triethylamine. Fractions shown by TLC to contain the desired material were combined, and the solvent removed by evaporation. Chromatography of the residue over SiO$_2$ using a 98:2 chloroform/methanol eluant yielded 645 mg of a yellow oil consisting of purified D-1-(1-propenyl)-6-n-propyl-8β-methylthiomethylergoline; nmr (CDCl$_3$): δ at 1.845 (Jab=7.03 Hz, Jac=1.76 Hz, side chain methyl, 3H); 5.38 (Jab=7.03 Hz, Jbc=8.68 Hz, one H, side chain β carbon), 6.78 (Jca=1.76 Hz, Jcb=8.68 Hz, one H, side chain α carbon). The nmr spectrum indicated conclusively the presence of a 1-propenyl group on the indole-ring nitrogen.

The base was converted to the methane sulfonate salt by the procedure of Example 1; MP=105°–120° C. (yield=137 mg from 301 mg base); Elemental analysis: Calculated: C, 61.30; H, 7.60; N, 6.22, 14.23; Found: C, 61.10; H, 7.34; N, 6.05, 14.15.

If the above procedure is carried out at −50° C. the 1-(2-propenyl) derivative is prepared; crude yield of free base=100%; nmr (CDCl$_3$)δ at 4.65 (2H, α CH$_2$), 5.1 (2H β CH$_2$); 5.9 (1H β). The nmr spectrum is consistent with the presence of an allyl group.

The methanesulfonate salt of D-1-(2-propenyl)-6-n-propyl-8β-methylthiomethylergoline prepared as in Example 1 melted at 160.5°–162.5° C. with decomposition after recrystallization from ethyl acetate; yield=59%. Mass spectrum; 3.54 (M-96), 325 (M-125). Elemental analysis: Calculated: C, 61.30; H, 7.60; N, 6.22; Found: C, 61.52; H, 7.37; N, 6.18.

Other N-1 derivatives such as the 4-methoxybenzyl, the 4-hydroxybenzyl, ethyl, 2-chlorobenzyl, 3-methylbenzyl and the like can be prepared by the above procedure.

The preparation of pharmaceutically-acceptable acid addition salts of the compounds of this invention, particularly the methane sulfonate salt, is illustrated in the above examples. Generally speaking, an equivalent of the free base in a nonpolar organic solvent, such as ether, can be mixed with an equivalent of the acid, also in ether. The salt is usually insoluble in the solvent system and is recovered by filtration. Alternatively, a solution of an equivalent of the free base represented by I in a lower alkanol is mixed with an equivalent of the acid, also in solution in a lower alkanol. In this variation, the salt is recovered by evaporation of the solvent and purified by recrystallization.

The compounds of this invention are dopamine agonists and thus useful in treating Parkinsonism, in inhibiting prolactin secretion; in reducing blood pressure, in treating sexual dysfunction etc—see for example U.S. Pat. No. 4,470,990 for uses of dopamine D-2 agonists. The laboratory model for determining the ability of a drug to inhibit prolactin secretion and thus be useful in treating gallactorrhea and inappropriate lactation, is as follows:

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep the rat prolactin levels uniformly elevated. The compound was dissolved in 10 percent ethanol, and injected intraperitoneally at a dose of 50 mcg/kg to a group of 10 rats. A control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats, gives the percent inhibition of prolactin secretion attributable to the given dose.

The compounds of this invention have also been found to affect turning behavior in 6-hydroxydopaminelesioned rats in a test procedure designed to uncover drugs useful for the treatment of Parkinsonism. In this test, nigroneostriatal-lesioned rats are employed, as prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period.

The compounds of this invention are also effective in the treatment of hypertension. Such activity is demonstrated in a standard laboratory test; ie., upon administration to SHR (spontaneously hypertensive rats). The compounds do not interact with receptors at dose levels at which they significantly lower blood pressure.

Table 1 which follows gives the results of the above determinations for compounds of this invention. In the table column 1 gives the R substituent in formula I above, column 2, the percent inhibition of prolactin secretion at a 50 mcg/kg drug dose i.p, column 3, turns in a 15 minute period at a 1 mg/kg drug dose i.p. and column 4, maximum percent change in mean arterial blood pressure with the i.v. drug dose in mcg/kg in parenthesis. Pergolide (R=H) is included as a control. At the 10 μg/kg dose level tested in SHR, pergolide reduces blood pressure satisfactorily, but at the next higher dose level, 100 μg/kg, it is a pressor substance. The compounds of this invention maintain their blood pressure lowering activity at increasing dose levels.

TABLE 1

| R | % Prolactin Inhibition | No of Turns | max % change |
|---|---|---|---|
| $CH_3$ | 81 | 86 | −21.0 (100) |
| n-$C_3H_7$ | 92 | 25 | −19.5 (100) |
|  |  |  | −31.6 (1000) |
| isopropyl | 85 | 44 | −37.0 (1000) |
| 1-propenyl | 91 | 69 | −13.1 (100) |
| 2-propenyl (allyl) | 85 | 25 | −13.5 (10) |
|  |  |  | −13.4 (1000) |
| benzyl | 79 | 28 | −20.1 (1) |
|  |  |  | −23.1 (10) |
|  |  |  | −52.3 (100) |
| 4-hydroxybenzyl | 84 | 33 | −24.2 (1000) |
| 4-methoxybenzyl | 20 | 23 | −15.8 (1000) |
| Control |  |  |  |
| H | 85 | 85 | −12.5 (10) |
|  |  |  | +15.0 (100) |

Activity in affecting sexual behavior by the compounds according to I above is demonstrated by measuring mount latency, intromission latency, ejaculatory latency, postejaculatory interval, mount frequency and intromission frequency in male rats who require at least five minutes to achieve ejaculation when a sexually receptive female is introduced into the behavioral arena prior to drug treatment. Reduction in one or more of the above indicia indicates a positive effect on sexual behaviour in male mammals including, but not limited to, improving potency. Sexually unresponsive male rats can also be used in such tests. Positive effects upon the sexual behaviour of female mammals are found when drugs according to I above are administered to ovariectomized, estrogen-treated rats, and the lordosis-to-mount ratio measured. An increase indicates a positive effect to be expected in female mammals suffering from a sexual dysfunction.

The compounds of this invention are usually administered for therapeutic purposes in a variety of oral formulations as illustrated below.

Hard gelatin capsules are prepared using the following ingredients:

|  | Quantity (mg./capsule) |
|---|---|
| Active compound | .1-20 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
|---|---|
| Active compound | .1-20 mg |
| Cellulose, microcrystalline | 400 |
| Silicon dioxide, fumed | 10 |
| Stearic acid | 5 |

The components are blended and compressed to form tablets.

Alternatively, tablets each containing 0.1-2 mg. of active ingredient are made up as follows:

| Active ingredient | .1-20 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed with a tablet machine to yield tablets.

Capsules each containing 0.1-2 mg. of medicament are made as follows:

| Active ingredient | .1-20 mg. |
|---|---|
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 0.1-2 mg. of medicament per 5 ml. dose are made as follows:

| Active ingredient | .1-20 mg. |
|---|---|
| Sodium carboxymethyl cellulose | 50 mg. |
| Syrup | 1.25 ml. |
| Benzoic acid solution | 0.10 ml. |
| Flavor | q.v. |

| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added with stirring. Sufficient water is then added to produce the required volume.

For oral administration in treating endocrine disorders such as sexual dysfunction, improving potency, alleviation the symptoms of Parkinsonism or inhibiting prolactin release, tablets, capsules or suspensions containing from about 0.1 to about 2 mg. of active drug per dose are given 3–4 times a day, giving a daily dosage of 0.3 to 8 mgs. or, for a 75 kg. person, about 2.25 to about 600 mg./per day. The intravenous dose is in the range from about 0.1 to about 100 mcg./kg. For oral administration in treating CNS disorders such as lowering blood pressure or treating depression or anxiety, dose levels of from 1.0–20 mg per kg are employed with a concomitant 10-fold increase in daily dose levels.

I claim:

1. A method of lowering blood pressure in hypertensive mammals which comprises administering to a hypertensive mammal in need of treatment a blood pressure lowering dose of a compound of the formula

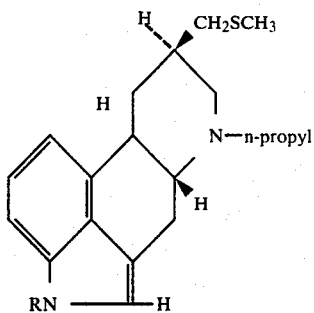

wherein R is 1-propenyl, 2-propenyl (allyl), $C_{1-3}$ alkyl, benzyl or substituted benzyl, wherein said substituents are one or two members of the class $C_{1-2}$ alkyl, $C_{1-2}$ alkoxy, hydroxy, Cl, Br, and F; and pharmaceutically-acceptable acid addition salts thereof.

2. A method according to claim 1 in which D-1-benzyl-6-n-propyl-8$\beta$-methylthiomethylergoline is the drug employed.